United States Patent [19]
Verma et al.

[11] Patent Number: 6,013,516
[45] Date of Patent: *Jan. 11, 2000

[54] VECTOR AND METHOD OF USE FOR NUCLEIC ACID DELIVERY TO NON-DIVIDING CELLS

[75] Inventors: Inder Verma, Solana Beach; Didier Trono, San Diego; Luigi Naldini, Del Mar; Philippe Gallay, Solana Beach, all of Calif.

[73] Assignee: The Salk Institute for Biological Studies, La Jolla, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/540,259

[22] Filed: Oct. 6, 1995

[51] Int. Cl.$^7$ .................................................. C12N 15/00
[52] U.S. Cl. .......................... 435/325; 514/44; 424/93.21; 424/93.2; 435/69.1; 435/320.1; 435/455
[58] Field of Search .............................. 514/44; 424/93.1, 424/93.2; 435/235.1, 69.1, 172.3, 455, 325; 935/32, 52, 57, 6

[56] References Cited

U.S. PATENT DOCUMENTS

| | | | |
|---|---|---|---|
| 5,449,614 | 9/1995 | Danos et al. | 435/455 |
| 5,554,524 | 9/1996 | Temin et al. | 435/235.1 |
| 5,580,766 | 12/1996 | Mason et al. | 435/455 |
| 5,686,279 | 11/1997 | Finer | 435/455 |
| 5,747,307 | 5/1998 | Lever | 435/455 |
| 5,750,396 | 5/1998 | Yang et al. | 435/357 |
| 5,817,491 | 10/1998 | Yee et al. | 435/455 |

FOREIGN PATENT DOCUMENTS

| | | |
|---|---|---|
| WO 91/05860 | 5/1991 | WIPO . |
| WO 91/19798 | 12/1991 | WIPO . |
| WO 93/17118 | 9/1993 | WIPO . |
| WO 93/20220 | 10/1993 | WIPO . |

OTHER PUBLICATIONS

Crystal, Science, vol. 270, pp. 404–410, 1995.
Dalgleish et al. (Virology, 165, 1988, pp. 209–215).
Landau et al. (J. Virology, vol. 65, No. 1, 1991, pp. 162–169).
Buchschacher et al. (J. Virology, vol. 66, 5:2731–2739, 1992).
Burn et al. (PNAS, vol. 90, Sep. 1993, pp. 8033–8037).
Kim et al. (Virology, 198,336–340, 1994).
Lusso et al., Science, vol. 247, pp. 848–852, 1990.
Ledley, FD. Clinical considerations in the design of protocols for somatic gene therapy. Human Gene Therapy 2:77–83, 1991.
Orkin, SH et al. Report and recommendations of the panel to assess the NIH investment in gene therapy. Issued by National Institutes of Health, Dec. 7, 1995.
Landau, NR et al. Pseudotyping with human T–cell leukemia virus type 1 broadens the human immunodeficiency virus host range. J. Virol. 65:162–169, 1991.

Jon Cohen, New Role for HIV: A Vehicle for Moving Genes into Cells., *Science* 272:195 (Apr. 12, 1996).
Bukrinsky et al., A Nuclear Localization Signal Within HIV–1 Matrix Protein That Governs Infection of Non–Dividing Cells., *Nature.*, 365:666–669 (Oct. 14, 1993).
Carroll et al., A Human Immunodeficiency Virus Type 1 (HIV–1)– Based Retroviral Vector System Utilizing Stable HIV–1 Packaging Cell Lines., *Journal Of Virology.*, 68(9):6047–6051 (Sep. 1994).
Gallay et al., HIV–1 Infection of Nondividing Cells: C–Terminal Tyrosine Phosphorylation of the Viral Matrix Protein is a Key Regulator., *Cell.*, 80:379–388 (Feb. 10, 1995).
Heinzinger et al., The Vpr Protein of Human Immunodeficiency virus type 1 influences Nuclear Localization of Viral Nucleic Acids in Nondividing Host Cells., *Biochemistry.*, 91:7311–7315 (Jul. 1994).
Lewis et al., Human Immunodeficiency Virus Infection of Cells Arrested in the Cell Cycle., *The EMBO Journal.*, 11(8):3053–3058 (1992).
Page et al., Construction and Use of Human Immunodeficiency Virus Vector for Analysis of Virus Infectivity., *Journal of Virology.*, 64(11):5270–5276 (Nov. 1990).
Poznansky et al., Gene Transfer into Human Lymphocytes by a Detective Human Immunodeficiency Virus Type 1 Vector., *Journal Of Virology.*, 65(1):532–536 (Jan. 1991).
Richardson et al., Helper Virus–Free Transfer of Human Immunodeficiency Virus Type 1 Vectors., *Journal of General Virology.*, 76:691–696 (1995).
Schwedler et al., The Nuclear Localization Signal of the Matrix Protein of Human Immunodeficiency Virus Type 1 Allows the establishment of infection in Macrophages and Quiescent T Lymphocyted., *Proc. Natl. Acad. Sci.*, 91:6992–6996 (Jul. 1994).
Trona et al., HIV–1 Gag Mutants Can Dominantly Interfere with the Replication of the Wild–Type Virus., *Cell.*, 59:113–120 (Oct. 6, 1989).
Naldini et al., "In Vivo Delivery and Stable Transduction of Nondividing Cells by a Lentiviral Vector", *Science*, vol. 272, Apr. 12, 1996, pp. 263–267.
Lewis et al., "Human Immunodeficiency Virus Infection of Cells Arrested in the Cell Cycle", *Oxford University Press*, pp. 3053–3058, received on Mar. 20, 1992; revised May 6, 1992.
Heinzinger et al., "The Vpr protein of human immunodeficiency virus type 1 influences nuclear localization of viral nucleic acids in nondividing host cells", *Proc. Natl. Acad. Sci., USA*, vol. 91, pp. 7311–7315, Jul. 1994, Biochemistry.
Bukrinsky et al., "A nuclear localization signal within HIV–1 matrix protein that governs infection of non–dividing cells", *Letters to Nature*, vol. 365, Oct. 14, 1993, pp. 666–669.

*Primary Examiner*—Scott D. Priebe
*Assistant Examiner*—Dave Trong Nguyen
*Attorney, Agent, or Firm*—Gray Cary Ware & Freidenrich LLP; Lisa A. Haile

[57] ABSTRACT

A recombinant retrovirus capable of infecting a non-dividing cell and a method of producing such a virus is provided. The recombinant retrovirus is preferably of lentivirus origin and is useful for the treatment of a variety of disorders including neurological disorders and disorders of other non-dividing cells.

6 Claims, 7 Drawing Sheets

FIG. 1

PURIFICATION AND CONCENTRATION OF VECTOR PARTICLES

| transfectant | infectious titer on 208F fibroblasts I.U./ml | | yeild |
|---|---|---|---|
| | conditioned medium | purified stock | |
| pCMVDR8\ pHR'ClacZ \ VSV.G | 6 10⁵ | 3.5 10⁸ | 30% |
| PCMVGAGPOL(MLV) pSLX-CLacZ \ VSV.G | 10⁵ | 3 10⁸ | 25% |

FIG. 2

TRANSDUCTION OF E.Coli β-GALACTOSIDASE GENE (LacZ) DRIVEN BY CMV PROMOTER

| co-transfection in 293T cells | | | | |
|---|---|---|---|---|
| packaging construct | | plasmid carrying CMV-LacZ | Env-encoding plasmid | infection of rat 208F cells I.U./ml |
| HIV-based | — | pHR' | MLV (Ampho) | 0 (<1/ml) |
| | pCMVDR8 | pHR' | — | 0 |
| | pCMVDR8 | pHR' | MLV (Ampho) | $10^5$ |
| | pCMVDR8 | pHR' | MLV (Eco) | $10^4$ |
| | pCMVDR8 | pHR' | VSV.G | $5\ 10^5$ |
| | pCMVDR8 | pLNL-SLX | MLV (Ampho) | 0 |
| | pCMVDR8 | pGEM | MLV (Ampho) | 0 |
| MLV-based | pCL-ECO | pLNL-SLX | | $10^5$ |
| | pCL-ECO | pHR' | | 0 |
| | pCMVGAGPOL | pLNL-SLX | MLV (Ampho) | $10^5$ |

SEQUENCE LISTING

<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: oligonucleotide for PCR

<400> SEQUENCE: 1
gtgaacggat ccttggcact atc                                              23

<210> SEQ ID NO 2
<211> LENGTH: 33
<212> TYPE: DNA
<213> ORGANISM: Artificial Sequence
<220> FEATURE:
<223> OTHER INFORMATION: oligonucleotide for PCR

<400> SEQUENCE: 2
cggggcggcc gctcagcagt tcttgaagta ctc                                   33

<210> SEQ ID NO 3
<211> LENGTH: 55
<212> TYPE: DNA
<213> ORGANISM: Artificial Sequence
<220> FEATURE:
<223> OTHER INFORMATION: oligonucleotide for PCR

<400> SEQUENCE: 3
ccggagtact tcaagaactg ctgagcggcc gccccggtga ccttcagacc ttggc           55

```
<210> SEQ ID NO 4
<211> LENGTH: 34
<212> TYPE: DNA
<213> ORGANISM: Artificial Sequence
<220> FEATURE:
<223> OTHER INFORMATION: oligonucleotide for PCR

<400> SEQUENCE: 4
gcggtctaga ctaagaaacc attattatca tgac                            34

<210> SEQ ID NO 5
<211> LENGTH: 45
<212> TYPE: DNA
<213> ORGANISM: Artificial Sequence
<220> FEATURE:
<223> OTHER INFORMATION: oligonucleotide for PCR

<400> SEQUENCE: 5
aagaccaccg cacagcaagc ggccgctgac acaggacaca gcaat                45
```

VECTOR AND METHOD OF USE FOR NUCLEIC ACID DELIVERY TO NON-DIVIDING CELLS

This invention was made with Government support from grant no. ROI AI37510 and CA 44360 awarded by the National Institutes of Health. The Government has certain rights in the invention.

FIELD OF THE INVENTION

The present invention relates generally to the field of viral vectors and specifically to a novel recombinant retrovirus useful for the transfer and expression of nucleic acid sequences in non-dividing cells.

BACKGROUND OF THE INVENTION

The development of genetic vectors has heralded the fast-growing field of somatic gene transfer. Vectors based on simple retroviruses, such as the Moloney Leukemia Virus (MLV), are often selected because they efficiently integrate into the genome of the target cell. Integration is thought to be a prerequisite for long-term expression of the transduced gene. However, currently available retroviral vectors can only integrate in actively dividing cells which severely limits their use for in vivo gene transfer. Non-dividing cells are the predomninant, long-lived cell type in the body, and account for most desirable targets of gene transfer, including liver, muscle, and brain. Even protocols attempting the transduction of hematopoietic stem cells require demanding ex vivo procedures for triggering cell division in these cells prior to infection.

In the early steps of infection, retroviruses deliver their nucleoprotein core into the cytoplasm of the target cell. Here, reverse transcription of the viral genome takes place while the core matures into a preintegration complex. The complex must reach the nucleus to achieve integration of the viral DNA into the host cell chromosomes. For simple retroviruses (oncoretroviruses), this step requires the dissolution of the nuclear membrane at mitotic prophase, most likely because the bulky size of the preintegration complex prevents its passive diffusion through the nuclear pores.

While retroviral vectors are useful for many kinds of in vitro gene transfer studies, problems including low titers limits their use for some in vitro and most in vivo studies. Further, another problem is that integration of retroviral vectors into the host genome was thought to be restricted to cells undergoing DNA replication. Thus, although retroviral vectors capable of infecting a broad class of cell types are known, cell division is necessary for the proviral integration of these vectors. This effectively restricts the efficient use of retrovirus vectors to replicating cells. Thus, retroviruses have not been utilized to introduce genes into non-dividing or post-mitotic cells.

A possible way around this obstacle was suggested by recent studies of the pathogenesis of lentiviral diseases. Lentiviruses are complex retroviruses, which, in addition to the common retroviral genes gag, pol, and env, contain other genes with regulatory or structural function. The higher complexity enables the virus to modulate its life cycle, as in the course of latent infection. A typical lentivirus is the Human Immunodeficiency Virus (HIV), the etiologic agent of AIDS. In vivo, HIV can infect macrophages which are terminally differentiated cells that rarely divide. In vitro, HIV can infect primary cultures of monocyte-derived macrophages (MDM), and HeLa-Cd4 or T lymphoid cells arrested in the cell cycle by treatment with aphidicolin or γ irradiation. Infection of these cells is dependent on the active nuclear import of HIV preintegration complexes through the nuclear pores of the target cells. This occurs by the interaction of multiple, partly redundant, molecular determinants in the complex with the nuclear import machinery of the target cell. Identified determinants include a functional nuclear localization signal (NLS) in the gag MA protein, the karyophilic virion-associated protein vpr, and a C-terminal phosphotyrosine residue in a subset of the gag MA protein.

SUMMARY OF THE INVENTION

The present invention provides a recombinant retrovirus that infects non-dividing host cells and transfers nucleic acid sequences which can then be expressed in the host cell. Thus, the present invention solves a long-felt need for a means of delivery of nucleic acid sequences to non-dividing cells.

In a first embodiment, the invention provides a recombinant retrovirus capable of infecting a non-dividing cell comprising a viral GAG, a viral POL, a viral ENV, a heterologous nucleic acid sequence operably linked to a regulatory nucleic acid sequence, and cis-acting nucleic acid sequences necessary for reverse transcription and integration. The recombinant retrovirus of the invention is preferably a lentivirus.

In another embodiment, the invention provides a method of producing a recombinant retrovirus capable of infecting a non-dividing cell comprising transfecting a suitable host cell with the following: a vector providing a nucleic acid encoding a viral gag and a viral pol, a vector providing a nucleic acid encoding a viral env, a vector providing a nucleic acid sequence encoding a packaging signal flanked by cis-acting nucleic acid sequences for reverse transcription and integration, and providing a cloning site for introduction of a heterologous nucleic acid sequence, operably linked to a regulatory nucleic acid sequence, and recovering the recombinant virus.

In yet another embodiment, the invention provides a method for introduction and expression of a heterologous nucleic acid sequence in a non-dividing cell comprising infecting the non-dividing cell with the recombinant virus of the invention and expressing the heterologous nucleic acid sequence in the non-dividing cell.

DESCRIPTION OF THE PREFERRED EMBODIMENTS

The present invention provides a recombinant retrovirus capable of infecting non-dividing cells. The virus is useful for the in vivo and ex vivo transfer and expression of genes nucleic acid sequences (e.g., in non-dividing cells).

Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences enabling encapsidation without coincident production of a contaminating helper virus. As described below, a helper virus is not required for the production of the recombinant retrovirus of the present invention, since the sequences for encapsidation are provided by co-transfection with appropriate vectors.

The retroviral genome and the proviral DNA have three genes: the gag, the pol, and the env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication. Lentiviruses have additional genes including vit vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site) If the sequences necessary for encapsidation (or packaging of retroviural RNA into infectious virions) are missing from the viral genome, the result is a cis defect which prevents encapsidation of genomic RNA. However, the resulting mutant is still capable of directing the synthesis of all virion proteins.

In a first embodiment, the invention provides a recombinant retrovirus capable of infecting a non-dividing cell. The recombinant retrovirus comprises a viral GAG, a viral POL, a viral ENV, a heterologous nucleic acid sequence operably linked to a regulatory nucleic acid sequence, and cis-acting nucleic acid sequences necessary for packaging, reverse transcription and integration, as described above. It should be understood that the recombinant retrovirus of the invention is capable of infecting dividing cells as well as non-dividing cells.

The recombinant retrovirus of the invention is therefore genetically modified in such a way that some of the structural, infectious genes of the native virus have been removed and replaced instead with a nucleic acid sequence to be delivered to a target non-dividing cell. After infection of a cell by the virus, the virus injects its nucleic acid into the cell and the retrovirus genetic material can integrate into the host cell genome. The transferred retrovirus genetic material is then transcribed and translated into proteins within the host cell.

Figure 1:
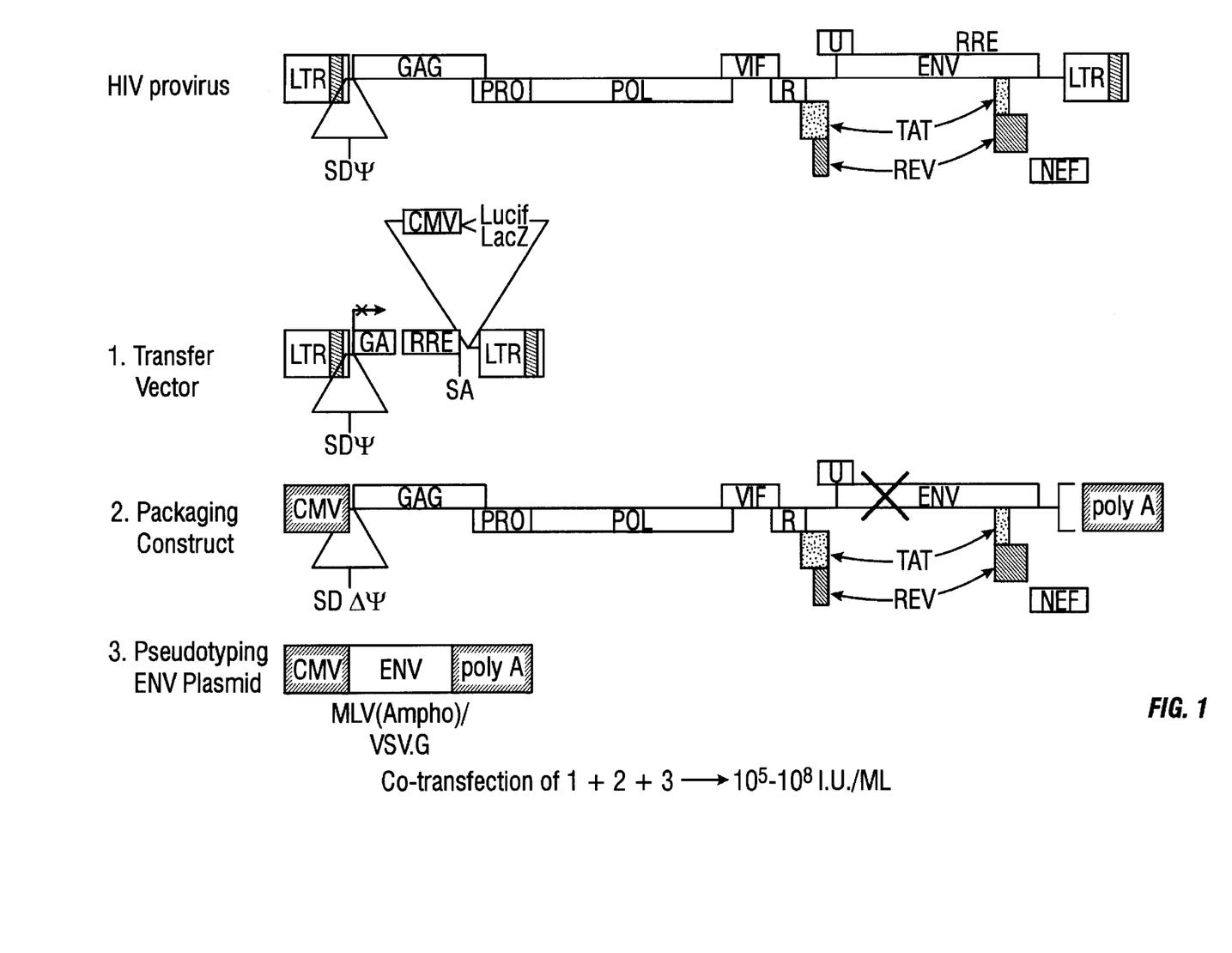
FIG. 1 is a schematic illustration of the method for production of an HIV-based recombinant retrovirus.

The invention provides a method of producing a recombinant retrovirus capable of infecting a non-dividing cell comprising transfecting a suitable host cell with the following: a vector providing a nucleic acid encoding a viral gag and a viral pol; a vector providing a nucleic acid encoding a viral env; a vector providing a nucleic acid sequence encoding a packaging signal flanked by cis-acting nucleic acid sequences for reverse transcription and integration, and providing a cloning site for introduction of a heterologous gene, operably linked to a regulatory nucleic acid sequence, and recovering the recombinant virus. An illustration of the individual vectors used in the method of the invention is shown in FIG. 1.

The method of the invention includes the combination of a minimum of three vectors in order to produce a recombinant virion or recombinant retrovirus. A first vector provides a nucleic acid encoding a viral gag and a viral pol. (see the illustrative Packaging Construct, FIG. 1) These sequences encode a group specific antigen and reverse transcriptase, (and integrase and protease-enzymes necessary for maturation and reverse transcription), respectively, as discussed above. Most preferably, the viral gag and pol are derived from a lentivirus, and most preferably from HIV.

A second vector provides a nucleic acid encoding a viral envelope (env). The env gene can be derived from any virus, including retroviruses. The env may be amphotropic envelope protein which allows transduction of cells of human and other species, or may be ecotropic envelope protein, which is able to transduce only mouse and rat cells. Further, it may be desirable to target the recombinant virus by linkage of the envelope protein with an antibody or a particular ligand for targeting to a receptor of a particular cell-type. By inserting a sequence (including regulatory region) of interest into the viral vector, along with another gene which encodes the ligand for a receptor on a specific target cell, for example, the vector is now target specific. Retroviral vectors can be made target specific by inserting, for example, a glycolipid, or a protein. Targeting is often accomplished by using an antibody to target the retroviral vector. Those of skill in the art will know of, or can readily ascertain without undue experimentation, specific methods to achieve delivery of a retroviral vector to a specific target.

Examples of retroviral-derived env genes include, but are not limited to: Moloney murine leukemia virus (MoMuLV), Harvey murine sarcoma virus (HaMuSV), murine mammary tumor virus (MuMTV), gibbon ape leukemia virus (GaLV), human immunodeficiency virus (HIV) and Rous Sarcoma Virus (RSV). Other env genes such as Vesicular stomatitis virus (VSV) (Protein G) can also be used.

The vector providing the viral env nucleic acid sequence is operably associated with regulatory sequence, e.g., a promoter or enhancer. (see Pseudotyping ENV plasmid, FIG. 1) Preferably, the regulatory sequence is a viral promoter. The regulatory sequence can be any eukaryotic promoter or enhancer, including for example, the Moloney murine leukemia virus promoter-enhancer element, the human cytomegalovirus enhancer (as used in the illustrative example), or the vaccinia P7.5 promoter. In some cases, such as the Moloney murine leukemia virus promoter-enhancer element, these promoter-enhancer elements are located within or adjacent to the LTR sequences.

A third vector provides the cis-acting viral sequences necessary for the viral life cycle. Such sequences include the ψ packaging sequence, reverse transcription signals, integration signals, viral promoter, enhancer, and polyadenylation sequences. The third vector also contains a cloning site for a heterologous nucleic acid sequence to be transferred to a non-dividing cell. A schematic illustration of a suitable vector is shown in FIG. 1).

Since recombinant retroviruses produced by standard methods in the art are defective, they require assistance in order to produce infectious vector particles. Typically, this assistance is provided, for example, by using a helper cell line that provides the missing viral functions. These plasmids are missing a nucleotide sequence which enables the packaging mechanism to recognize an RNA transcript for encapsidation. Helper cell lines which have deletions of the packaging signal include but are not limited to ψ2, PA317 and PA12, for example. Suitable cell lines produce empty virions, since no genome is packaged. If a retroviral vector is introduced into such cells in which the packaging signal is intact, but the structural genes are replaced by other genes of interest, the vector can be packaged and vector virion produced.

The method of producing the recombinant retrovirus of the invention is different than the standard helper virus/ packaging cell line method described above. The three or more individual vectors used to co-transfect a suitable packaging cell line collectively contain all of the required genes for production of a recombinant virus for infection and transfer of nucleic acid to a non-dividing cell. Consequently, there is no need for a helper virus.

The heterologous nucleic acid sequence is operably linked to a regulatory nucleic acid sequence. As used herein, the term "heterologous" nucleic acid sequence refers to a sequence that originates from a foreign species, or, if from the same species, it may be substantially modified from its original form. Alternatively, an unchanged nucleic acid sequence that is not normally expressed in a cell is a heterologous nucleic acid sequence. The term "operably linked" refers to functional linkage between the regulatory sequence and the heterologous nucleic acid sequence. Preferably, the heterologous sequence is linked to a promoter, resulting in a chimeric gene. The heterologous nucleic acid sequence is preferably under control of either the viral LTR promoter-enhancer signals or of an internal promoter, and retained signals within the retroviural LTR can still bring about efficient integration of the vector into the host cell genome.

The promoter sequence may be homologous or heterologous to the desired gene sequence. A wide range of promoters may be utilized, including viral or mammalian promoter. Cell or tissue specific promoters can be utilized to target expression of gene sequences in specific cell populations. Suitable mammalian and viral promoters for the present invention are available in the art.

Preferably during the cloning stage, the nucleic acid construct referred to as the transfer vector, having the packaging signal and the heterologous cloning site, also contains a selectable marker gene. Marker genes are utilized to assay for the presence of the vector, and thus, to confirm infection and integration. The presence of this marker gene ensures the growth of only those host cells which express the inserts. Typical selection genes encode proteins that confer resistance to antibiotics and other toxic substances, e.g. histidinol, puromycin, hygromycin, neomycin, methotrexate, etc. The illustrative examples herein utilize the β-galactosidase (LacZ) or luciferase reporter or marker system.

The recombinant virus of the invention is capable of transferring a nucleic acid sequence into a non-dividing cell. The term nucleic acid sequence refers to any nucleic acid molecule, preferably DNA. The nucleic acid molecule may be derived from a variety of sources, including DNA, cDNA, synthetic DNA, RNA, or combinations thereof. Such nucleic acid sequences may comprise genomic DNA which may or may not include naturally occurring introns. Moreover, such genomic DNA may be obtained in association with promoter regions, introns, or poly A sequences. Genomic DNA may be extracted and purified from suitable cells by means well known in the art. Alternatively, messenger RNA (mRNA) can be isolated from cells and used to produce cDNA by reverse transcription or other means.

The phrase "non-dividing" cell refers to a cell that does not go through mitosis. Non-dividing cells may be blocked at any point in the cell cycle, (e.g., $G_0/G_1$, $G_1/S$, $G_2/M$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). The recombinant retrovirus vector of the invention is capable of infecting any non-dividing cell, regardless of the mechanism used to block cell division or the point in the cell cycle at which the cell is blocked. Examples of pre-existing non-dividing cells in the body include neuronal, muscle, liver, skin, heart, lung, and bone marrow cells, and their derivatives.

Preferably, the recombinant retrovirus produced by the method of the invention is lentivirus-derived, and more preferably the recombinant lentivirus is a derivative of human immunodeficiency virus (HIV). For public policy reasons, typically when the retrovirus is HIV, the env will be derived from a virus other than HIV.

The method of the invention provides at least three vectors which provide all of the functions required for packaging of recombinant virions as discussed above. The method also envisions transfection of vectors including viral genes such as vpr, vif, nef, vpx, tat, rev, and vpu. Some or all of these genes can be included on the packaging construct vector, for example, or, alternatively, they may reside on individual vectors. There is no limitation to the number of vectors which are utilized, as long as they are co-transfected to the packaging cell line in order to produce a single recombinant retrovirus. For example, one could put the env nucleic acid sequence on the same construct as the gag and pol.

The vectors are introduced via transfection or infection into the packaging cell line. The packaging cell line produces viral particles that contain the vector genome. Methods for transfection or infection are well known by those of skill in the art. After co-transfection of the at least three vectors to the packaging cell line, the recombinant virus is recovered from the culture media and titered by standard methods used by those of skill in the art.

In another embodiment, the invention provides a recombinant retrovirus produced by the method of the invention as described above.

The invention also provides a recombinant retrovirus capable of infecting a non-dividing cell comprising a viral GAG; a viral POL; a viral ENV; a heterologous nucleic acid sequence operably linked to a regulatory nucleic acid sequence; and cis-acting nucleic acid sequences necessary for packaging, reverse transcription and integration. The recombinant retrovirus is preferably a lentivirus, and most preferably HIV. As described above for the method of producing a recombinant retrovirus above, the recombinant retrovirus of the invention may further include at least one of VPR, VIF, NEF, VPX, TAT, REV, and VPU protein. While not wanting to be bound by a particular theory, it is believed that one or more of these genes/protein products are important for increasing the viral titer of the recombinant retrovirus produced (e.g., NEF) or may be necessary for infection and packaging of virions, depending on the packaging cell line chosen (e.g. VIF).

The invention also provides a method of nucleic acid transfer to a non-dividing cell to provide expression of a particular nucleic acid sequence. Therefore, in another embodiment, the invention provides a method for introduction and expression of a heterologous nucleic acid sequence in a non-dividing cell comprising infecting the non-dividing cell with the recombinant virus of the invention and expressing the heterologous nucleic acid sequence in the non-dividing cell.

It may be desirable to modulate the expression of a gene regulating molecule in a cell by the introduction of a molecule by the method of the invention. The term "modulate" envisions the suppression of expression of a gene when it is over-expressed, or augmentation of expression when it is under-expressed. Where a cell proliferative disorder is associated with the expression of a gene, nucleic acid sequences that interfere with the gene's expression at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, *Anal.Biochem.*, 172:289, 1988).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinsonism, and other diseases. Antisense nucleic acids are also useful for the inhibition of expression of proteins associated with toxicity.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anti-cancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.*,260:3030, 1988). A major advantage of this approach is that, because they are sequence-specific, only mRNAs with particular sequences are inactivated.

It may be desirable to transfer a nucleic acid encoding a biological response modifier. Included in this category are immunopotentiating agents including nucleic acids encoding a number of the cytokines classified as "interleukins". These include, for example, interleukins 1 through 12. Also included in this category, although not necessarily working according to the same mechanisms, are interferons, and in particular gamma interferon ($\gamma$-IFN), tumor necrosis factor (TNF) and granulocyte-macrophage-colony stimulating factor (GM-CSF). It may be desirable to deliver such nucleic acids to bone marrow cells or macrophages to treat enzymatic deficiencies or immune defects. Nucleic acids encoding growth factors, toxic peptides, ligands, receptors, or other physiologically important proteins can also be introduced into specific non-dividing cells.

The recombinant retrovirus of the invention can be used to treat an HIV infected cell (e.g., T-cell or macrophage) with an anti-HIV molecule. In addition, respiratory epithelium, for example, can be infected with a recombinant retrovirus of the invention having a gene for cystic fibrosis transmembrane conductance regulator (CFTR) for treatment of cystic fibrosis.

The method of the invention may also be useful for neuronal or glial cell transplantation, or "grafting", which involves transplantation of cells infected with the recombinant retrovirus of the invention ex vivo, or infection in vivo into the central nervous system or into the ventricular cavities or subdurally onto the surface of a host brain. Such methods for grafting will be known to those skilled in the art and are described in *Neural Grafting in the Mammalian CNS*, Bjorklund and Stenevi, eds., (1985), incorporated by reference herein. Procedures include intraparenchymal transplantation, (i.e., within the host brain) achieved by injection or deposition of tissue within the host brain so as to be apposed to the brain parenchyma at the time of transplantation.

Administration of the cells or virus into selected regions of the recipient subject's brain may be made by drilling a hole and piercing the dura to permit the needle of a microsyringe to be inserted. The cells or recombinant retrovirus can alternatively be injected intrathecally into the spinal cord region. A cell preparation infected ex vivo, or the recombinant retrovirus of the invention, permits grafting of neuronal cells to any predetermined site in the brain or spinal cord, and allows multiple grafting simultaneously in several different sites using the same cell suspension or viral suspension and permits mixtures of cells from different anatomical regions.

Cells infected with a recombinant retrovirus of the invention, in vivo, or ex vivo, used for treatment of a neuronal disorder for example, may optionally contain an exogenous gene, for example, a gene which encodes a receptor or a gene which encodes a ligand. Such receptors include receptors which respond to dopamine, GABA, adrenaline, noradrenaline, serotonin, glutamate, acetylcholine and other neuropeptides, as described above. Examples of ligands which may provide a therapeutic effect in a neuronal disorder include dopamine, adrenaline, noradrenaline, acetylcholine, gamma-aminobutyric acid and serotonin. The diffusion and uptake of a required ligand after secretion by an infected donor cell would be beneficial in a disorder where the subject's neural cell is defective in the production of such a gene product. A cell genetically modified to secrete a neurotrophic factor, such as nerve growth factor, (NGF), might be used to prevent degeneration of cholinergic neurons that might otherwise die without treatment. Alternatively, cells be grafted into a subject with a disorder of the basal ganglia, such as Parkinson's disease, can be modified to contain an exogenous gene encoding L-DOPA, the precursor to dopamine. Parkinson's disease is characterized by a loss of dopamine neurons in the substantia-nigra of the midbrain, which have the basal ganglia as their major target organ.

Other neuronal disorders that can be treated similarly by the method of the invention include Alzheimer's disease, Huntington's disease, neuronal damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic cells infected with a recombinant retrovirus of the invention containing an exogenous gene for a factor which would promote survival of these neurons can be accomplished by the method of the invention, as described. Following a stroke, there is selective loss of cells in the CA1 of the hippocampus as well as cortical cell loss which may underlie cognitive function and memory loss in these patients. Once identified, molecules responsible for CA1 cell death can be inhibited by the methods of this invention. For example, antisense sequences, or a gene encoding an antagonist can be transferred to a neuronal cell and implanted into the hippocampal region of the brain.

The method of transferring nucleic acid also contemplates the grafting of neuroblasts in combination with other therapeutic procedures useful in the treatment of disorders of the CNS. For example, the retroviral infected cells can be co-administered with agents such as growth factors, gangliosides, antibiotics, neurotransmitters, neurohormones, toxins, neurite promoting molecules and antimetabolites and precursors of these molecules such as the precursor of dopamine, L-DOPA.

Further, there are a number of inherited neurologic diseases in which defective genes may be replaced including: lysosomal storage diseases such as those involving β-hexosaminidase or glucocerebrosidase; deficiencies in hypoxanthine phosphoribosyl transferase activity (the "Lesch-Nyhan" syndrome"); amyloid polyneuropathies (-prealbumin); Duchenne's muscular dystrophy, and retinoblastoma, for example.

For diseases due to deficiency of a protein product, gene transfer could introduce a normal gene into the affected tissues for replacement therapy, as well as to create animal models for the disease using antisense mutations. For example, it may be desirable to insert a Factor IX encoding nucleic acid into a retrovirus for infection of a muscle of liver cell.

The following Examples are intended to illustrate, but not to limit the invention. While such Examples are typical of those that might be used, other procedures known to those skilled in the art may alternatively be utilized.

EXAMPLES

The following examples illustrate the three-plasmid lentiviral vector system of the invention. A non infectious plasmid provides in trams the structural and regulatory proteins of HIV but the envelope (packaging construct, pCMVΔR8). The transducing vector contains all known cis-acting sequences of HIV-and cloning sites for the introduction of the gene to be transduced (vector plasmid, pHR'). In the experiments described hereafter, two marker genes (E. coli β-galactosidase -LacZ-, and firefly luciferase -Lucif-), driven by the human Cytomegalovirus immediate early enhancer/promoter -CMV or C- have been cloned in the vector plasmid, thus generating pHR'CLacZ and pHR'-Clucif FIG. 1).

A third plasmid encodes a heterologous envelope to pseudotype the viral particles. Pseudotyping both broadens the host range of the vector, and increases its biosafety. Three types of env-encoding plasmid have been used in the present examples. Plasmid pSV-A-MLV-env (Page, et al., 1990, J Virol., 64:5270, 1990) encodes the amphotropic envelope of the 4070 Moloney Leukemia Virus (MLV/Ampho) under the transcriptional control of the MLV LTR. Plasmid pCMV-Eco env encodes the ecotropic envelope of the Moloney Leukemia Virus (MLV/Eco) under the transcriptional control of the CMV promoter (N. Somia, Salk Institute, La Jolla, Calif.). Plasmid pMD.G encodes the envelope protein G of the Vescicular Stomatitis Virus (VSV.G) under the transcriptional control of the CMV promoter (D. Ory and R. Mulligan, Whitehead Institute, Cambridge, Mass.).

Replication-defective viral particles were produced by the transient co-transfection of the three plasmids in 293T human kidney cells. The conditioned medium was harvested, filtered, and assayed for the transduction of the reporter genes into target cells by standard methods. Human HeLa cells and rat 208F fibroblasts were tested in different growth conditions, and the dependence of the transduction on the progression along the cell cycle was evaluated. Growth arrest by density-dependent inhibition of growth (GO) was compared with pharmacological or other means of the cell cycle arrest (later phases of the cycle). The transduction of non-dividing, terminally differentiated cells such as macrophages and neurons was also tested, both in vitro and in vivo.

Example 1

Construction of pCMVΔR8

The packaging plasmid pCMVDR8 was constructed in a series of steps starting from the plasmid pR8, an infectious molecular clone of proviral HIV DNA. pR8 was made by replacing a BamHl-BssHll fragment in the plasmid pR7 (Kim et al., J. Virol., 63:3708, 1989; von Schwedler et al., J. Virol., 67:4945, 1993), which contains the HIV-1 HXB2d proviral DNA (Shaw et al., Science, 226:1165, 1984) with a full-length nef reading frame, by the homologous fragment from the NL4.3 HIV proviral DNA. NL4.3 is a molecularly constructed provirus that contains full-length, functional vpr and vpu reading frames (Adachi et al., J. Virol., 59:284, 1986). The backbone of plasmid pR7/R8 contains the Amp resistance gene and the pUC origin of replication from plasmid sp65, and the SV40 origin of replication and the gpt gene from plasmid pSVgpt. An env-defective version of pR8, pΔER8, was made by replacing the 2.7 kbp SalI-BamHI fragment with the homologous fragment from pΔER7, which contains a MluI linker inserted at the StuI site 6831 that frameshifts the env reading frame (Trono, et al., Cell., 59:113, 1989). A 39 bp internal deletion in the Ψ sequence between the 5' splice donor site and the starting codon of the gag gene, was introduced in pΔER8 by replacing a 797 bp BssHII-SpeI fragment with an homologous 758 fragment containing a previously described deletion in the packaging signal (Aldovini & Young, J. Virol., 64:1920, 1990). The resulting plasmid was called pΔΨER8. Plasmid pAΔΨΔER8 was constructed by replacing the 3' HIV LTR with the polyadenylation site of insulin genomic DNA (Trono, et al., Cell., 59:113, 1989) maintaining intact the nef reading frame. It was constructed by PCR, introducing a unique NotI site at the junction between the nef reading frame and the polyA signal.

In a first series of amplification, a 961 bp fragment was amplified with the oligonucleotides gp41.4 (s), overlapping the BamHI site in gp41 of HIV1HXB2- and nef27 (a) from the pΔER8 template, and a 402 bp fragment was amplified with the oligonucleotides LN-A(s) and LN-B (a) containing an XbaI site—from a DNA template containing the polyadenylation site of the insulin gene. Oligonucleotides nef27 (a) and LN-A(s) contain a complementary sequence carrying a NotI restriction site. The two amplificates were purified, mixed and used as template for a second amplification with the oligonucleotides gp41.4(s) and LN-B(a) (see Table 1 for oligo sequences). The final 1.3 kbp product was purified, digested with BamHI and XbaI and cloned in the 13.5 kpb BamHI-XbaI fragment of pΔΨΔER8. Plasmid pCMVΔ8 was constructed substituting the 5' LTR and leader sequences in pAΔΨΔER8 with the CMV promoter. A 0.8 kbp fragment containing the CMV promoter was lifted from the plasmid pCMVpA (W. W. Chang, University of Texas, M. D. Anderson Cancer Center, Houston, Tex.) by double digestion with SmaI and HpaI. A MluI linker was added to the HpaI ends and the fragment was cloned into the 14.5 kbp BssH1I-HpaI fragment of pAΔΨΔER8. One of skill in the art will be able to identify similar starting plasmids and sequences without undue experimentation based on the teachings herein.

TABLE 1

| Oligonucleotide | Nucleotide sequence |
|---|---|
| gp41.4 (s) | (SEQ ID NO:1)<br>5' GTGAACGGATCCTTGGCACTATC 3' |
| nef 27 (a) | (SEQ ID NO:2)<br>5' CGGGGCGGCCGCTCAGCAGTTCT TGAAGTACTC 3' |
| LN-A (s) | (SEQ ID NO:3)<br>5' CCGGAGTACTTCAAGAACTGCTGA GCGGCCGCCCCGGTGACCTTCAGA CCTTGGC 3' |
| LN-B (a) | (SEQ ID NO:4)<br>5' GCGGTCTAGACTAAGAAACCATTATTA TCATGAC 3' |
| gag31 (s) | (SEQ ID NO:5)<br>5' AAGACCACCGCACAGCAAGCGGC CGCTGACACAGGACACAGCAAT 3' |

Example 2

Construction of pHR'

The vector plasmid pHR' was constructed by cloning a fragment of the env gene encompassing the RRE (responsive element) and a splice acceptor site between the two LTR's of the HIV-1 HXB2 proviral DNA. The leader and Ψ sequences were retained in the construct, together with the 5' 0.3 kbp of the gag gene, previously shown to constitute an extended packaging signal. A 854 bp env fragment (BglII 7620-BamHI 8474) was obtained from pR7. A NotI linker was added to the filled-in BglII end. The fragment was cloned into the 8.9 kbp NotI-BamHI fragment of plasmid pMAKK[113]TTR7, a pR7 derivative containing mutations in the gag codons 113, 114, and 118 (the last ones introduce a unique NotI cloning site; sequence as in oligonucleotide Gag 31 (s)). Plasmid pHR was obtained. Plasmid pHR' was generated introducing a frameshift mutation 42 bp downstream the gag gene AUG, which closes the reading frame of the gene fragment retained in the construct. The mutation was introduced by opening and filling-in a ClaI site. Two unique BamHI and XhoI sites are available in pHR' upstream of the 3' LTR for cloning inserts.

Example 3

Construction of pHR'-CLacZ and pHR'-Clucif

A SalI-XhoI 3.6 kbp fragment containing the E. coli β-galactosidase gene under the trascriptional control of the CMV promoter was obtained from the plasmid pSLX-CMVLacZ (Scharfmann et al., Proc. Natl. Acad Sci. USA, 88:4626, 1991). After filling-in the SalI ends, the fragment was cloned into the 8.9 kbp XhoI-BamHI fragment of pHR', whose BamHI ends had previously been filled-in. pHR'-ClacZ was obtained. pHR'-CLucif was obtained replacing a 3.1 kbp BamHI-XhoI fragment in pHR'-CLacZ, containing the LacZ reading frame, with a 1.7 kbp BamHI-Xhol fragment from pGEM-luc (Promega) containing the firefly luciferase reading frame.

Example 4

Production of Vector Particles

Replication-defective viral particles were produced by the transient cotransfection of the above-described plasmids in 293T human kidney cells. All plasmids were transformed and grown in E. coli HB101 bacteria following standard molecular biology procedures. For transfection of eukaryotic cells, plasmid DNA was purified twice by equilibrium centrifugation in CsCl-ethidium bromide gradients. A total of 40 µg DNA was used for the transfection of a culture in a 10 cm dish, in the following proportions: 10 µg pCMVΔR8, 20 µg pHR', and 10 µg env plasmids, either MLV/Ampho, MLV/Eco or VSV.G. When a plasmid was omitted, or added in different proportion, pGEM-LacZ was added to maintain constant the total amount of DNA added to the cells. 293T cells were grown in DMEM supplemented with 10% fetal calf serum and antibiotics in a 10% $CO_2$ incubator. Cells were plated at a density of $1.3 \times 10^6/10$ cm dish the day before transfection. Culture medium was changed 4 to 6 hrs before transfection. Calcium phosphate-DNA complexes were prepared according to the method of Chen and Okayama (Mol. Cell. Biol., 7:2745, 1987), and incubated overnight with the cells in an atmosphere of 5% $CO_2$. The following morning, the medium was replaced, and the cultures returned to 10% $CO_2$. Conditioned medium was harvested 48 to 60 hrs after transfection, cleared of cellular debris by low speed centrifugation (300×g 10 min), and filtered through 0.45 µm low protein binding filters. The conditioned medium was either used immediately for infection or kept frozen at −80° C. The content of viral particles was monitored by p24 gag antigen ELISA (DuPont).

MLV-based vectors were also produced from transient cotransfection in 293T cells of the following plasmids. Plasmid pSLX-CMVLacZ (Scharfmann et al., Proc. Natl. Acad. Sci. USA, 88:4626, 1991) is a MLV-derived vector carrying a CMV-driven E. coli β-galactosidase gene. The pCL plasmid series carry a hybrid CMV-LTR promoter which allows for CMV-driven transcription in the packaging cell and reconstitution of a functional LTR in the target cell (R. Naviaux, Salk Institute, La Jolla, Calif.). Plasmid pCLNC-Lucif is a MLV-derived vector carrying a CMV-driven Firefly luciferase gene. It was made by cloning a 1.7 kbp HindIII-StuI fragment from pGEM-luc (Promega), containing the luciferase reading frame, into the 8 kbp ClaI-HindIII fragment of pCLNCX, after filling-in the ClaI ends. Plasmid pCL-ECO is a ecotropic packaging plasmid. Plasmid pCMV-GAGPOL (N. Somia, Salk Institute, La Jolla, Calif.) is a semi-packaging plasmid carrying a CMV-driven gag-pol gene from MLV. It was used in conjunction with pMD.G to package VSV.G-pseudotyped MLV-based vectors.

Figure 2:
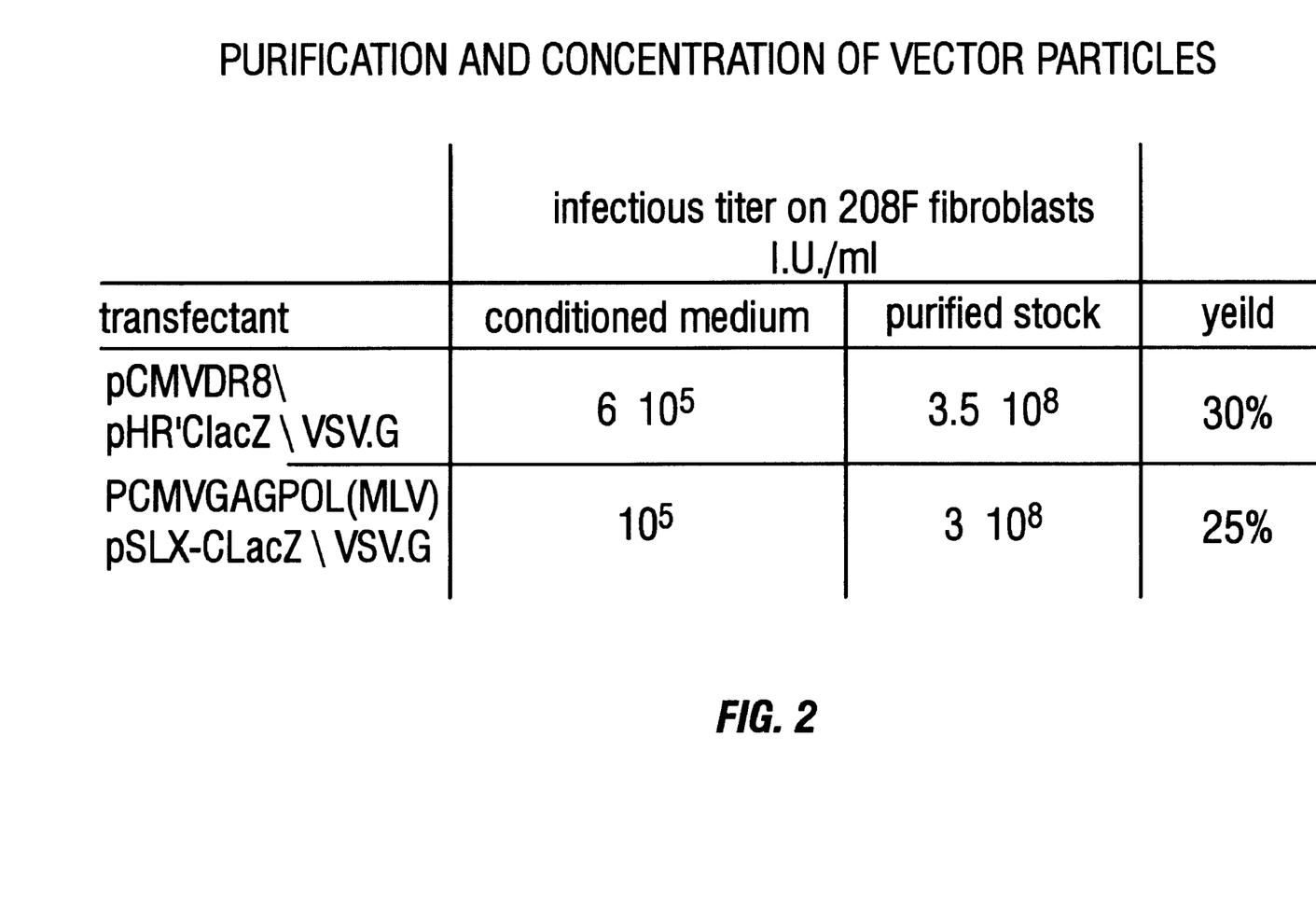
FIG. 2 is a table of the titer of infectious virus particles using a VSV.G env, LacZ reporter gene and a packaging construct having an HIV (pCMVDR8) or MLV gag/pol before and after concentration (="yield").

FIG. 2 shows a comparison between the infectious titers of recombinant lentivirus (HIV) construct and an MLV construct assayed on 208F fibroblasts. The results indicate that the HIV vector of the present invention is at least as infectious as the standard MLV vector. Purified stock indicated that titers after concentrating the supernatant by ultracentrifugation. Yield reflects percent recovery of virus after concentration.

Figure 3:
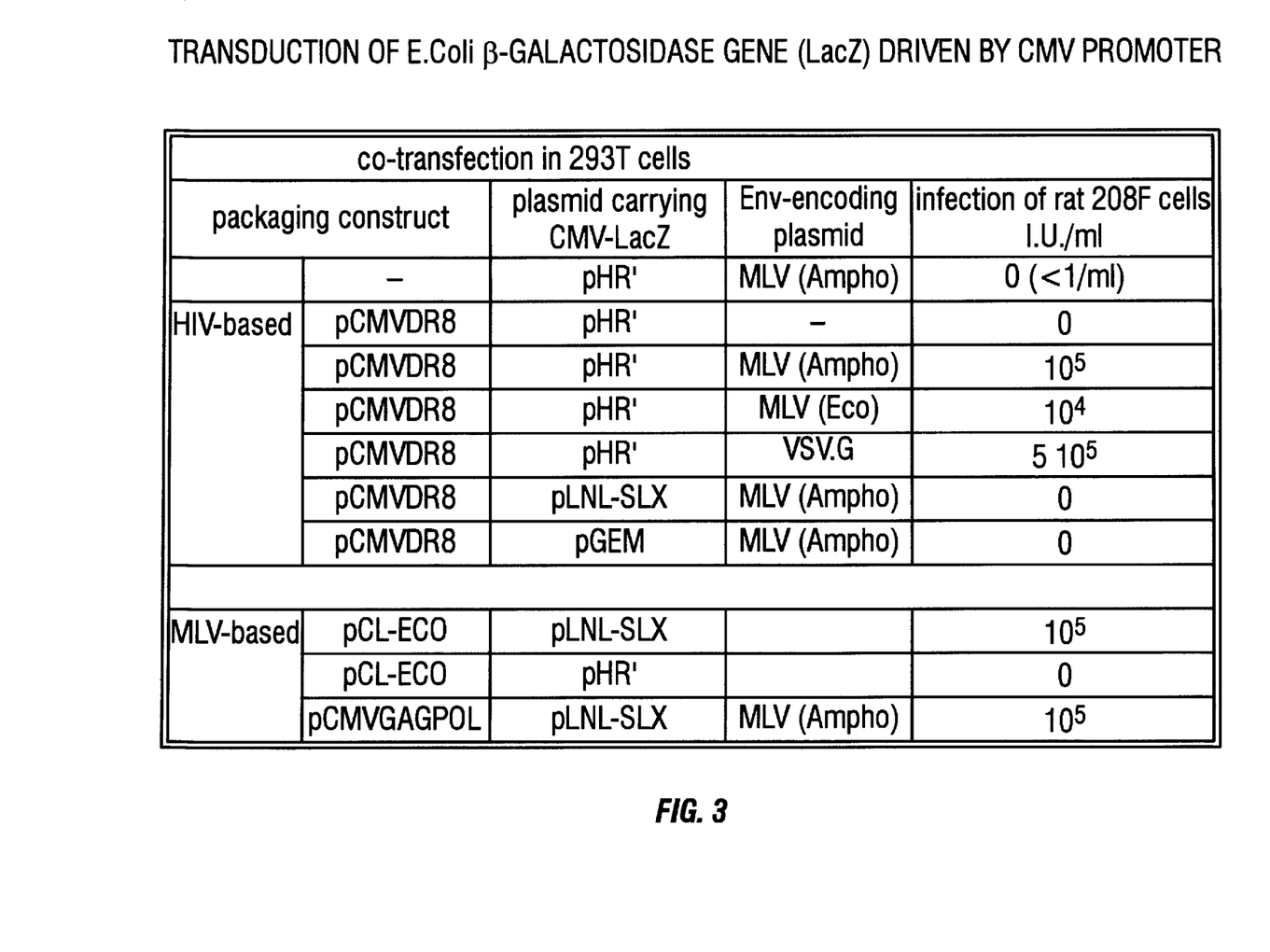
FIG. 3 is a table of titers of recombinant virus after co-transfection of 293T cells (fibroblast packaging cell line) with HIV-based and MLV-based packaging constructs.

FIG. 3 shows the results of co-transfection of a packaging construct, env-encoding construct and transfer vector (as in FIG. 1). Various HIV and MLV-based packaging constructs were compared using amphotropic and ecotropic env genes, as well as VSV.G env. The figure shows a comparison of infection of rat 208F cells with the resulting recombinant retroviruses. The titers for the HIV constructs having an MLV (amphotropic) or VSV.G env were similar to the standard MLV-based vector (approximately $10^5$). The infectious titer for the HIV-based construct having an MLV ecotropic env was about 10-fold less than the amphotropic env (approx. $10^4$).

Example 5

Concentration of Viral Particles

Pooled conditioned medium harvested as described above was layered on top of a cushion of 20% sucrose solution in PBS and centrifuged in a Beckman SW28 rotor at 50,000×g for 90 min. The pellet was resuspended by incubation and gentle pipetting in 1–4 ml PBS for 30–60 min, then centrifuged again at 50,000×g×90 min in a Beckmann SW55 rotor. The pellet was resuspended in a minimal volume (20–50 $\mu$l) of PBS and either used directly for infection or stored in frozen aliquots at −80° C.

Example 6

Infection of Cultured Cells

For the infection of cultured cells, serial dilutions of conditioned medium from 293T transient transfectants or of concentrated viral stocks were added to the culture medium supplemented with 8 $\mu$g/ml polybrene. The cells were incubated from 3 hrs to overnight, then the medium was replaced, and the cells further incubated for 36 hrs prior to assaying expression of the transduced gene. Expression of $\beta$-Galactosidase ($\beta$-Gal) was scored by fixing the cultures 5 min in cold 2% formaldehyde/0.2% glutaraldehyde in PBS, washing twice with PBS, and staining with 1 mg/ml X-gal in PBS containing 5 mM each of K ferri- and ferro-cyanide and 2 mM $MgCl_2$, for 4 hrs to overnight at 37° C. Titers were calculated counting the number of individual foci of blue cells per well, and multiplying it by the volume of vector stock added and the dilution factor. Expression of luciferase was assayed by washing the cultures twice with TBS and extracting the cells with 200 $\mu$l/well 0.5% NP40 in TBS containing 5 mM $MgCl_2$. The extract was cleared by centrifugation at 15,000×g for 10 min. 50 $\mu$l of extract were diluted with 150 $\mu$l of 75 mM Tris-HCl pH=7.8, 15 mM Mg acetate and 4 mM ATP, and assayed for luminescence in a luminometer which added 100 $\mu$l of 1 mM luciferin.

Human HeLa cells (ATCC) were grown in RPM1 1640–10% fetal calf serum in an atmosphere of 5% $CO_2$. For infection of dividing cultures, cells were seeded at a density of $1.6 \times 10^5$/well in a 6-well tray the day before infection. G1/S arrested cultures were prepared seeding $2 \times 10^5$ cells/well two days before infection, and adding 15 $\mu$g/ml aphidicolin 24 hrs before infection. Aphidicolin was added daily to the medium throughout the infection and post-infection time, as described. G2-arrested cells were prepared by exposing the cells for 20 min to a $^{61}$Co source calibrated at 200 rad/min one day before infection and seeding the cells at $4 \times 10^5$/well. Cell cycle arrest at the indicating stage of the cycle was confirmed by propidium iodide staining and flow cytometry.

Figure 4:
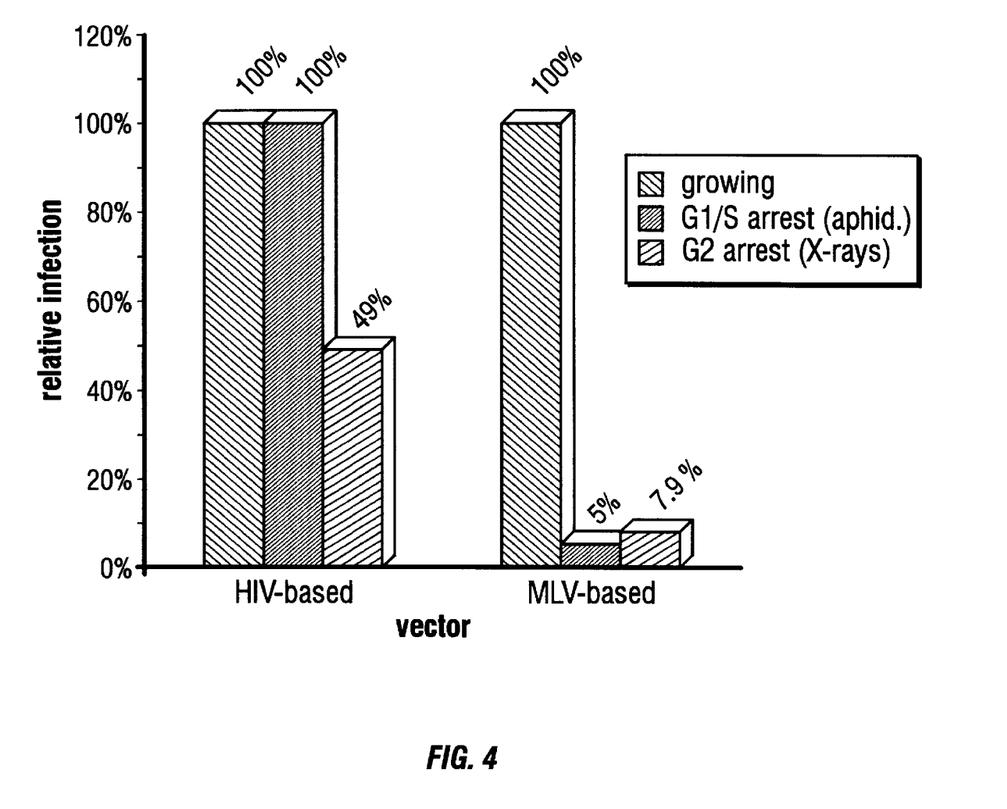
FIG. 4 is a graph of the efficiency of transduction of HIV and MLV-based CMV-β-galactosidase vectors into growing HeLa cells, cells arrested at the G1/S interphase by aphidicolin, and cells arrested at G2 by x-rays.

FIG. 4 shows the relative efficiency of transduction of CMV-$\beta$-Gal into HeLa cells. The cells were growth arrested using either pharmacological means (aphidicolin) or x-irradiation. The infection rate for the HIV-based vector was more efficient when cells were arrested at the G1/S interphase by aphidicolin, however, the HIV-based vector was more efficient than MLV-based vector overall.

Rat 208F fibroblasts (a gift of B. Sefton, Salk Institute, La Jolla, Calif.) were grown in DMEM-10% calf serum in an atmosphere of 10% $CO_2$. For infection of growing cultures, cells were seeded at a density of $10^5$ cells/well in a 6-well tray the day before infection. Growth-arrested cultures were prepared by seeding $2.5 \times 10^5$ cells/well in a 6-well tissue culture tray, and shifting the cultures to medium containing 5% calf serum and 2 $\mu$M dexamethazone after they reached confluence, as described by Miller et al. (Mol. Cell. Biol, 10:4239, 1990). Medium was changed every three-four days, and the cultures were kept for two to four weeks. When not otherwise indicated, $G_0$ cultures were used 3 weeks after reaching confluence. Growth arrest was documented by propidium iodide staining and flow cytometry. The fraction of cells in S-phase was 40 to 50% in growing cells, and from 10 down to 2% after reaching confluence, depending on the time past it. For rescue experiments, infected $G_0$ cultures were trypsinized at the indicated time after infection, and the cells replated at several dilutions. Expression of $\beta$-Gal was scored 48 hrs from replating.

Figure 5:
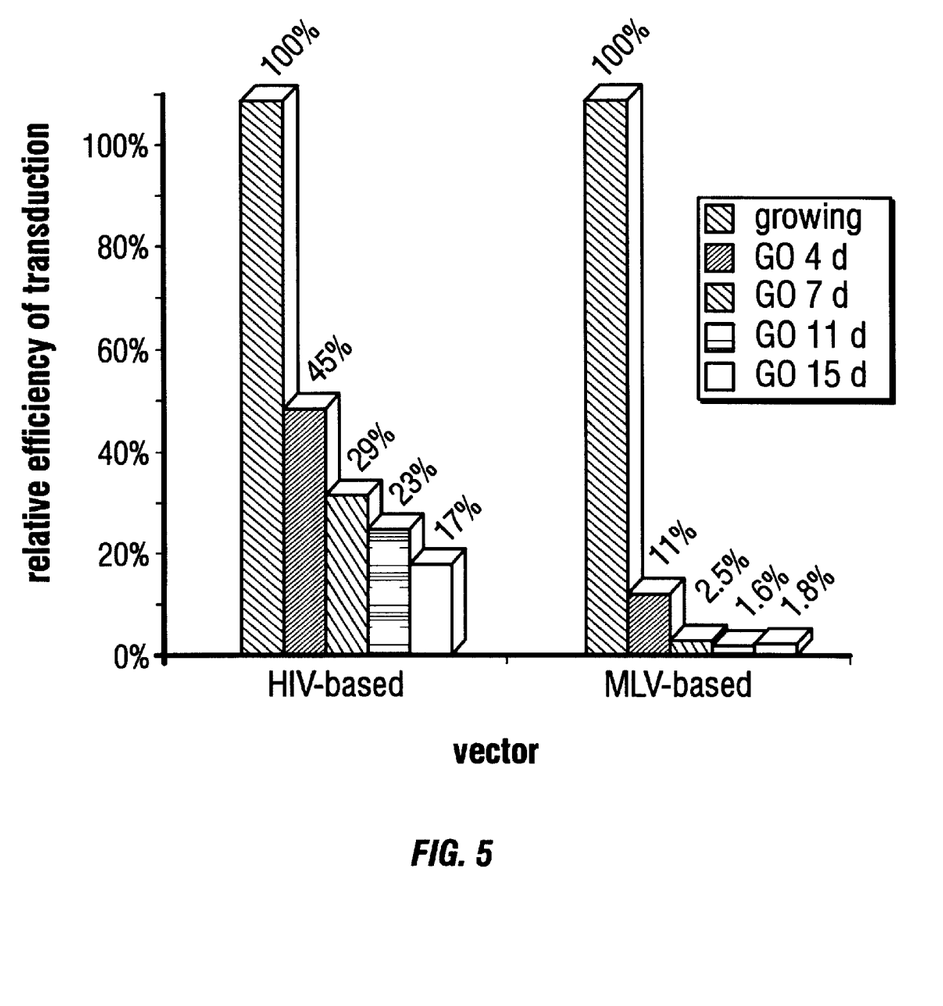
FIG. 5 is a graph of the efficiency of transduction of HIV and MLV CMV-luciferase vectors into rat 208F fibroblasts in G0 after 4, 7, 11, and 15 days.

FIG. 5 shows the relative efficiency of transduction of CMV-luciferase into rat 208F fibroblasts with the HIV- and MLV-based vectors in cells growth arrested for 4, 7, 11 or 15 days. The results show that the vectors both efficiently infect growing cells. The efficiency of transduction of the HIV-based vector versus the MLV-based vector was approximately 4–10 fold higher, depending on the length of time of the growth arrest.

Figure 6:
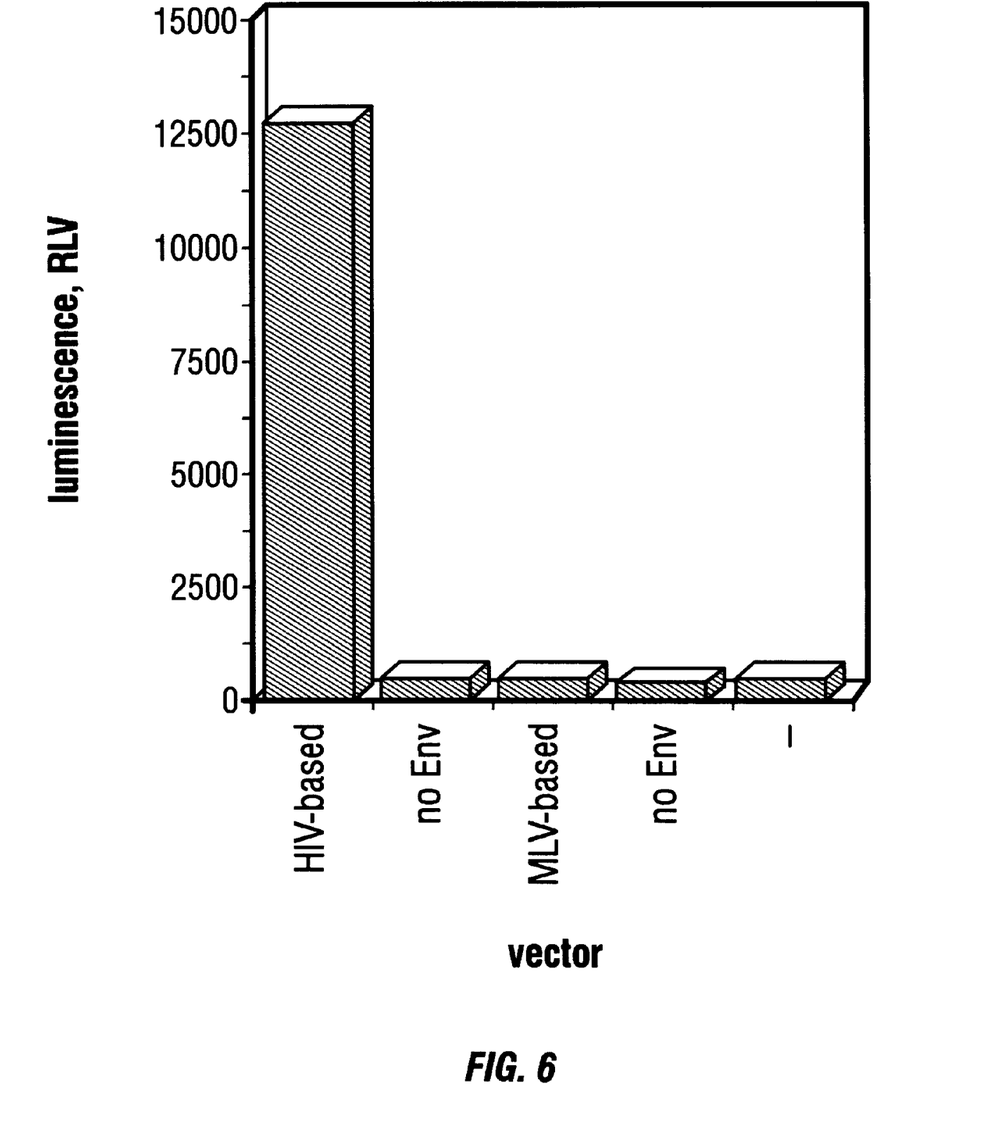
FIG. 6 is a graph of the efficiency of transduction of HIV and MLV CMV-luciferase vectors into human primary macrophages.

Human peripheral blood monocytes were prepared from the buffy coats of healthy donors as previously described (von Schwedler et al., Proc. Natl. Acad Sci. USA, 91:6992, 1994). Monocyte-derived macrophages were cultured in RPM1-10% human serum (Sigma) for two to four weeks prior to infection. FIG. 6 shows the results of transduction of CMV-luciferase into human primary macrophages using the HIV-based and MLV-based vectors, either with or without an envelope. The MLV-based vector was almost completely ineffective in infecting the cells and was similar in infectivity to the non-enveloped virus. In contrast, the HIV-based vector was highly efficient in transducing primary macrophages.

Figure 7:
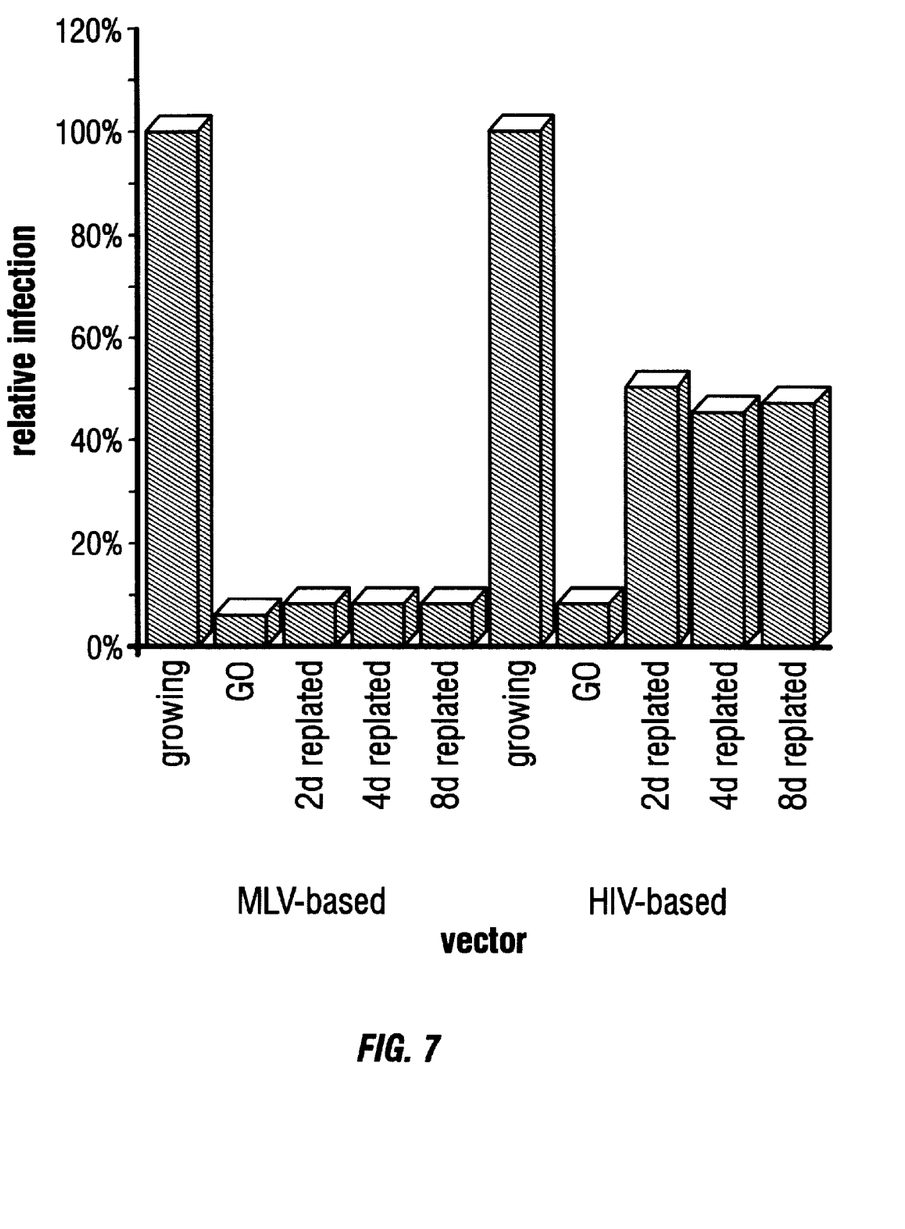
FIG. 7 is a graph of survival of HIV- and MLV-based vector in cells arrested for 3 weeks, inoculated with the vectors, and induced to divide at indicated times after infection.

Further, the survival of the HIV-based vector was assessed in growth arrested cells that were passaged over a period of 2–8 days. Survival of the MLV-based vector was very low in cells at G0 and after replating at 2, 4, and 8 days. However, the HIV-based vector maintained at about 45–50% infectivity in the same cells. While not wanting to be bound by a particular theory, it is believed that HIV can remain extrachromosomal without being degraded, unlike MLV. Therefore, HIV is stable without integration.

Example 7

Infection in vivo

For in vivo experiments, HIV-based and MLV-based vectors carrying a CMV-LacZ marker gene were used. Both vector types were pseudotyped with VSV.G envelope proteins. Vectors were purified and concentrated to a titer of 3×10⁸ I.U./ml in a vehicle of sterile PBS supplemented with 2 μg/ml polybrene. All procedures were performed according to institution-approved protocols for animal work, and in a biosafety level 3 (BSL3) environment. Normal adult female Fischer rats were anesthetized with a mixture of ketamine (44 mg/kg), acepromazine (0.75 mg/kg) and xylozine (4 mg/kg) in 0.9% NaCl. 2 μl of viral suspension were slowly injected in the corpus striatum of both sides of the brain with a stereotactical guide using a 5 μl Hamilton syringe with a 26 gauge beveled needle. 7 days after injection the rats were deeply anesthetized and perfused with 4% formaldehyde/0.1% glutaraldehyde. The brains were removed and free-floating coronal freezing microtome sections (40 μm) were processed in parallel series of one section out of every five cut. One series was processed for β-Gal immunocytochemistry with a monoclonal antibody and stained with avidin/biotin peroxidase and diaminobenzidine/$NiCl_2$ as substrate. Another series was processed for triple immunofluorescence with β-Gal (rabbit), NeuN (monoclonal), and GFAP (guinea pig) antibodies using FITC-, Texas Red-, or Cy5-labeled secondary antibodies. NeuN is a nuclear marker reported to be present in terminally differentiated neurons (Mullen, *Develop.*, 116:201, 1992). Glial fibrillar acidic protein (GFAP) is a astrocyte differentiation marker. The sections were then analyzed by confocal scanning laser microscopy (bioRad MRTC600). Immunofluorescent signals were collected, digitally color enhanced and superimposed. False color images were generated electronically using Adobe Photoshop (Adobe System Inc.).

The results revealed numerous β-gal positive neurons in regions injected with the HIV-based vector, but not in those inoculated with the MLV-based vector.

SUMMARY

The results indicated the feasibility of gene transfer using a lentiviral vector. Using growing cells, the transduction efficiency obtained with a three-plasmid, transient packaging system was comparable to that obtained with similarly assembled, conventional (MLV-based) retroviral vectors. In sharp contrast with MLV-based vectors, the lentiviral vector was capable of efficient gene transfer in the absence of division of the target cell. Efficiency of transduction into non-dividing cells in vitro was dependent on the stage of cell cycle arrest. Infection of G1/S and G2 arrested cells was as efficient as that observed with growing cells. Infection of cells arrested in $G_0$ in vitro was less efficient, the lesser the longer the cultures had been in $G_0$. However, in long-term $G_0$ cultures the vector survived as a stable intermediate, and it could be rescued to complete its infectious cycle by stimulation of the cells to divide. Transduction of the marker gene into terminally differentiated cells, such as human primary macrophages in vitro and rat cerebral neurons in vivo, was observed.

Although the invention has been described with reference to the presently preferred embodiment, it should be understood that various modifications can be made without departing from the spirit of the invention. Accordingly, the invention is limited only by the following claims.

---

What is claimed is:

1. A method of producing a lentivirus which infects non-dividing cells, said method comprising:
   a) transfecting a suitable packaging host cell with the following vectors:
      a first vector providing a nucleic acid encoding a lentiviral gag and a lentiviral pol wherein the gag and pol nucleic acid sequences are operably linked to a heterologous regulatory nucleic acid sequence and wherein the vector is defective for nucleic acid sequence encoding functional ENV protein and wherein the nucleic acid of the first vector is devoid of lentiviral sequences both upstream and downstream from a splice donor site to a gag initiation site of a lentiviral genome;
      a second vector providing a nucleic acid encoding a non-lentiviral ENV protein;
      a third vector providing a nucleic acid sequence containing a lentiviral packaging signal flanked by lentiviral cis-acting nucleic acid sequences for reverse transcription, packaging and integration; a heterologous nucleic acid sequence, operably linked to a regulatory nucleic acid sequence; and a less than full length gag structural gene; and
   b) recovering the recombinant virus.

2. The method of claim 1, wherein the lentivirus is human immunodeficiency virus (HIV).

3. The method of claim 1, wherein the first vector further includes at least a nucleic acid sequence operably linked to a promoter, wherein the nucleic acid sequence encodes a protein selected from the group consisting of VPR, VIF, NEF, VPX, TAT, REV, VPU and any combination thereof.

4. The method of claim 1, wherein the transfecting further includes providing a nucleic acid sequence of a fourth vector, wherein the nucleic acid sequence is operably linked to a promoter and encodes a protein selected from the group consisting of VPR, VIF, NEF, VPX, TAT, REV, VPU and any combination thereof.

5. The method of claim 1, wherein the less than a full length gag structural gene has a closed reading frame.

6. Three lentiviral vectors wherein a first vector comprises a nucleic acid encoding a lentiviral gag and a lentiviral pol wherein the gag and pol nucleic acid sequences are operably linked to a heterologous regulatory nucleic acid sequence and wherein the first vector is defective for nucleic acid sequence encoding functional ENV protein and nucleic acid of first the vector is devoid of lentiviral sequences both upstream and downstream from a splice donor site to a gag initiation site of a lentiviral genome; a second vector providing a nucleic acid encoding a non-lentiviral ENV protein; and a third vector providing a nucleic acid sequence containing a lentiviral packaging signal flanked by lentiviral cis-acting nucleic acid sequences for reverse transcription, packaging and integration; a heterologous nucleic acid sequence operably linked to a regulatory nucleic acid sequence; and a less than full length gag structural gene, wherein the third vector is devoid of one or more accessory genes, wherein the three vectors, when introduced into a host cell, express lentiviral proteins to form lentiviral virions that are replication defective.

* * * * *